United States Patent [19]

Nachtigal et al.

[11] 4,275,055

[45] Jun. 23, 1981

[54] HAIR CONDITIONER HAVING A STABILIZED, PEARLESCENT EFFECT

[75] Inventors: Julius H. Nachtigal, Edison; David C. Zajac, East Brunswick, both of N.J.

[73] Assignee: Conair Corporation, Edison, N.J.

[21] Appl. No.: 51,433

[22] Filed: Jun. 22, 1979

[51] Int. Cl.³ .............................................. A61K 7/06
[52] U.S. Cl. ...................................... 424/70; 424/322
[58] Field of Search .......................................... 424/70

[56] References Cited

U.S. PATENT DOCUMENTS

| | | | |
|---|---|---|---|
| 3,959,461 | 5/1976 | Bailey et al. | 424/70 |
| 3,990,991 | 11/1976 | Gerstein | 424/70 |
| 4,007,261 | 2/1977 | Sorrentino et al. | 424/70 |
| 4,035,478 | 7/1977 | Mullen | 424/70 |
| 4,061,150 | 12/1977 | Dasher et al. | 424/70 |

FOREIGN PATENT DOCUMENTS

| | | | |
|---|---|---|---|
| 1040750 | 10/1958 | Fed. Rep. of Germany | 424/70 |
| 701273 | 1/1931 | France | 424/70 |
| 1495547 | 7/1967 | France | 424/70 |

Primary Examiner—Dale R. Ore
Attorney, Agent, or Firm—Parmelee, Johnson, Bollinger and Bramblett

[57] ABSTRACT

A hair conditioner is provided having a stable pearlescent effect which is achieved in the absence of nacreous or synthetic pearlescing agents. In addition to the usual substances for controlling pH, for conditioning, for emulsifying, and for preserving, this hair conditioner also includes two conditioning agents which together serve to produce a pearlescent effect that remains stable and does not settle. These agents are preferably stearamidopropyl dimethyl benzylammonium chloride and stearyl dimethyl benzylammonium chloride in the ratios of about 2.5 to about 7.5% and about 2 to about 5%, by weight, respectively, together with about 0.25% to about 0.75% by weight of sodium chloride.

10 Claims, No Drawings

HAIR CONDITIONER HAVING A STABILIZED, PEARLESCENT EFFECT

BACKGROUND OF THE INVENTION

There are various nacreous and synthetic pigments which can impart an appearance of "pearlescence" or shimmery luster to cosmetic products. However, incorporation of these components in hair conditioning vehicles presents formulation difficulties. Specifically, the pearlescent effect often is only short-lived, and the materials settle out of the vehicle.

Accordingly, it is the purpose of the present invention to disclose hair conditioning formulations which contain cosmetically stable materials producing pearlescent effects. The system disclosed allows for the formulation of pearlescene without the settling normally observed; and the pearlescent effect is achieved in the absence of conventional pearlescing agents.

The hair conditioning compositions revealed are capable of providing not only a pearlized appearance, while at the same time rendering superior conditioning properties to the hair. The essential feature of these conditioning components is their ability to provide body, manageability, and detangling properties without displaying the greasiness, coating or gumminess normally associated with conventional conditioners. This causes the hair to retain its degree of cleanliness over a longer period of time.

The present formulations have been found cosmetically acceptable through an accelerated aging period of 3 months at 110° F., equivalent to an acceptable shelf-life expectancy. Furthermore, "beauty lab half-head tests" have indicated good response with regard to body, manageability, and detangling, as well as a lack of greasiness normally associated with hair conditioners.

DESCRIPTION OF THE INVENTION

The hair conditioner of this invention includes compounds to maintain the pH between 3.0 and 4.0, to provide emolliency and lubricity, to provide texture and shine, to provide for emulsification and proper viscosity to give anti-static qualities, and to act as preservatives. Various known compounds may be used for these purposes. The pearlescence, however, is not provided for by the addition of synthetic pearlescent materials which can settle, but by use of conditioning agents that, acting together, serve to create a stable pearlescent effect with a good shelf life.

Compositions of the present invention may contain by weight (a) from 2 to 5% of stearyl dimethyl benzylammonium chloride, and (b) 2.5 to 7.5% of a fatty dimethyl benzylammonium chloride in combination with (c) 0.40% to 0.75% of an ethylene diamine containing short-chain alkyl and long-chain alkoyl groups and (d) 0.25% to 0.75% sodium chloride, and (e) 0.30% to 1.5% of an emulsifying wax. Preferably, the four components are present at ratios of 3% stearyl dimethyl benzylammonium chloride, 5% of fatty dimethyl benzylammonium chloride, 0.60% of the ethylene diamine derivative, 0.5% sodium chloride, and, 1% of emulsifying wax. Furthermore, the preferred components are respectively: 3% of stearyl dimethyl benzylammonium chloride, 5% of stearamidopropyl dimethyl benzylammonium chloride, 0.60% of stearamidoethyl diethylamine and 1% of a primary emulsifier such as a Polawax, other conditioners, preservatives against microorganisms and perfume may be added.

The pearlescent effect appears to be created by an interaction of the following materials: stearamidopropyl dimethyl benzylammonium chloride, stearyl dimethyl benzylammonium chloride, and sodium chloride, in deionized water. The proportions of these compounds are preferably 5.00%, 3.00%, and 0.50%, by weight, respectively. The pearlescent effect can be obtained with use of other chlorides, as long as the quantity used is sufficient to provide a minimum viscosity of 3,000 centipoises.

A typical pearlescent hair conditioning composition illustrative of this invention is given in the following example.

EXAMPLE I

| Constituent | Weight Percent |
|---|---|
| Deionized Water | 77.05 |
| Citric Acid | 0.45 |
| Stearamidoethyl diethylamine | 0.60 |
| Propyl P-Hydroxybenzoate | 0.10 |
| Methyl P-Hydroxybenzoate | 0.20 |
| Stearamidopropyl dimethyl benzylammonium chloride | 5.00 |
| Stearyl dimethyl benzylammonium chloride | 3.00 |
| Cetyl/stearyl alcohol ethoxylate | 0.75 |
| Polyethylene glycol ether of cetearyl alcohol | 0.75 |
| Emulsifying Wax | 1.00 |
| Neutral Henna Extract | 10.00 |
| 1-(3-chloroallyl)-3,5,7-triaza-1-azoniaadamantane chloride | 0.10 |
| 1,3-dimethylol-5,5-dimethyl hydantoin | 0.25 |
| Sodium Chloride | 0.50 |
| Perfume | 0.25 |

This hair conditioner of Example I is made as follows (trade names, defined below, are used for simplicity):

Add deionized water to a proper vessel and begin heating. Then add citric acid and allow to mix. Then add chemical base 6532 and methyl paraben and propyl paraben and stir until completely dissolved. When temperature reaches 60°–80° C., add Richquat 150 and continue stirring. Then add Ammonyx 4 and Lipocol SC-4 and stir until batch is uniform. Then add Siponic E-3, and stir until batch is uniform. At this stage, product may turn opaque. Maintain temperature at 60°–80° C. and add Polawax, and stir for about 10 minutes. At this stage, product is opaque. Then add Neutral Henna Extract and allow the batch to mix 15 minutes before beginning to cool. Then begin cooling slowly until the temperature reaches 50° C. At 50° C., add preservatives with mixing. Then add sodium chloride and mix until completely dissolved. Cool batch slowly with continuous stirring until temperature reaches 40° C. Then add fragrance and allow to stir for an additional 10–15 minutes. Pearlescence appears at 35°–40° C.

Other examples are:

EXAMPLE II

| Constituent | Weight Percent |
|---|---|
| Deionized Water | 78.15 |
| Citric Acid | 0.45 |
| Stearamidoethyl diethylamine | 0.60 |
| Propyl P-Hydroxybenzoate | 0.10 |
| Methyl P-Hydroxybenzoate | 0.20 |
| Stearamidopropyl dimethyl benzylammonium chloride | 5.00 |
| Stearyl dimethyl benzylammonium chloride | 3.00 |

-continued

| Constituent | Weight Percent |
| --- | --- |
| Polyethylene Glycol Ether of Cetyl Alcohol | 0.75 |
| Emulsifying Wax | 1.00 |
| Neutral Henna Extract | 10.00 |
| 1-(3-chloroallyl)-3,5,7-triaza-1-azoniaadamantane chloride | 0.20 |
| Sodium Chloride | 0.30 |
| Perfume | 0.25 |

EXAMPLE III

| Constituent | Weight Percent |
| --- | --- |
| Deionized Water | 76.55 |
| Citric Acid | 0.45 |
| Stearamidoethyl Diethylamine | 0.60 |
| Propyl P-Hydroxybenzoate | 0.10 |
| Methyl P-Hydroxybenzoate | 0.20 |
| Stearamidopropyl Dimethyl Benzylammonium Chloride | 5.00 |
| Stearyl Dimethyl Benzylammonium Chloride | 3.00 |
| Cetyl/Stearyl Alcohol Ethoxylate | 0.75 |
| Polyethylene Glycol Ether of Cetearl Alcohol | 0.75 |
| Emulsifying Wax | 1.50 |
| Neutral Henna Extract | 10.00 |
| Imidazolidinyl Urea | 0.10 |
| 1,3-Dimethylol-5,5-Dimethyl Hydantoin | 0.25 |
| Sodium Chloride | 0.50 |
| Perfume | 0.25 |

EXAMPLE IV

| Constituent | Weight Percent |
| --- | --- |
| Deionized Water | 78.05 |
| Citric Acid | 0.45 |
| Stearamidoethyl diethylamine | 0.60 |
| Propyl P-Hydroxybenzoate | 0.10 |
| Methyl P-Hydroxybenzoate | 0.20 |
| Stearamidopropyl Dimethyl Benzylammonium Chloride | 2.50 |
| Stearyl Dimethyl Benzylammonium Chloride | 5.00 |
| Cetyl/Stearyl Alcohol Ethoxylate | 0.75 |
| Polyethylene Glycol Ether of Cetearyl Alcohol | 0.75 |
| Emulsifying Wax | 0.50 |
| Neutral Henna Extract | 10.00 |
| 1-(3-Chloroallyl)-3,5,7-triaza-1-azoniaadamantane Chloride | 0.10 |
| 1,3-Dimethylol-5,5-Dimethyl Hydantoin | 0.25 |
| Sodium Chloride | 0.50 |
| Perfume | 0.25 |

EXAMPLE V

| Constituent | Weight Percent |
| --- | --- |
| Deionized Water | 76.05 |
| Citric Acid | 0.45 |
| Stearamidoethyl Diethylamine | 0.60 |
| Propyl P-Hydroxybenzoate | 0.10 |
| Methyl P-Hydroxybenzoate | 0.20 |
| Stearamidopropyl Dimethyl Benzylammonium Chloride | 7.50 |
| Stearyl Dimethyl Benzylammonium Chloride | 2.00 |
| Cetyl/Stearyl Alcohol Ethoxylate | 0.75 |
| Polyethylene Glycol Ether of Cetearyl Alcohol | 0.75 |
| Emulsifying Wax | 0.50 |
| Neutral Henna Extract | 10.00 |
| 1-(3-Chloroallyl)-3,5,7-Triaza-1-Azoniaadamantane Chloride | 0.10 |
| 1,3-Dimethylol-5,5-Dimethyl Hydantoin | 0.25 |
| Sodium Chloride | 0.50 |
| Perfume | 0.25 |

The conditioners of Examples II through V are prepared in a manner similar to that of Example I.

Satisfactory pearlescence is obtained if the following constituents are kept within the following approximate ranges:

| | |
| --- | --- |
| Stearamidopropyl dimethyl benzylammonium chloride | 2.50% to 7.50% |
| Stearyl dimethyl benzyl-ammonium chloride | 2.00% to 5.00% |
| Sodium chloride | 0.25% to 0.75% | and preferably, though not necessarily, stearamidoethyl diethylamine is used in the range between about 0.40% and about 0.75%. Other constituents may vary as dictated by normal skill in the hair conditioning art.

Various of the above chemicals are available commercially under trade names of particular companies. These are given in the following table:

| Trade Name | Chemical Name |
| --- | --- |
| Ammonyx 4 (Onyx) | Stearyl dimethyl benzyl-ammonium chloride |
| BRIJ 52 (ICI) | Polyethylene glycol ether of cetyl alcohol |
| Chemical Base 6532 (Sandoz) | Stearamidoethyl diethylamine |
| DMDM Hydantoin (Glyco) | 1,3-dimethylol-5,5-dimethyl hydantoin |
| Dowicil 200 (DOW) | 1-(3-chloroallyl)-3,5,7-triaza-1-azoniaadamantane chloride |
| Germall 115 (Sutton Labs) | Imidazolidinyl urea |
| Lipocol SC-4 (Lipo Chemicals) | Cetyl/Stearyl alcohol ethoxylate |
| Methyl Paraben (Mallinckrodt) | Methyl P-hydroxybenzoate |
| Polawax (Croda, Inc.) | Emulsifying wax |
| Propyl Paraben (Mallinckrodt) | Propyl P-hydroxybenzoate |
| Richquat 150 (Richardson) | Stearamidopropyl dimethyl benzyl ammonium chloride |
| Siponic E-3 (Alcolac Chemical) | Polyethylene glycol ether of cetearyl alcohol |

It should be noted that pH is controlled by the amount of citric acid; that conditioning effects are provided by stearamidoethyl diethylamine, stearamidopropyl dimethyl benzylammonium chloride, stearyl dimethyl benzylammonium chloride and neutral henna extract; that cetyl/stearyl alcohol ethoxylate, polyethylene glycol ether of cetearyl alcohol and emulsifying wax are used as emulsifiers; that sodium chloride can serve to control viscosity; and that propyl p-hydroxybenzoate, methy p-hydroxybenzoate, 1-(3-chloroallyl)-3,5,7-triaza-1-azoniaadamantane chloride, 1,3-dimethylol-5,5-dimethyl hydantoin, and imidazolidinyl urea serve as preservatives against microorganisms.

Conditioning ingredients which may be used in place of stearamidoethyl diethylamine are:
Diethylaminoethyl Stearamide
Diethylaminopropyl Stearamide
Stearamidopropyl Dimethylamine
Stearamidopropyl Dimethylamine Lactate.

Acids which may be used in place of citric acid include:
Lactic Acid

Tartaric Acid
Gluconic Acid
Acetic Acid
Hydrochloric Acid
Phosphoric Acid.

In this respect, note that the quantity of acid used should be such as to keep the pH between about 3.0 and about 4.0.

There are various other emulsifiers commercially available which may be substituted for the emulsifiers used in the above formulations. Note, however, that the use of Polawax as the primary emulsifier in the present formulations, serves to enhance the pearlescent effect.

Note with respect to the hair conditioners of this invention that there are certain particular features of value:

(a) Formation of a "pearlized effect" in-situ by the interaction of Richquat 150, Ammonyx 4 and sodium chloride. Incorporation of conventional pearlescent agents is no longer required.

(b) In-situ interaction allows for the ultimate stabilization of the pearlized look through an acceptable shelf-life expectancy. Severe settling problems are no longer observed, and we have been able to achieve hair conditioning formulations which contain cosmetically stable pearlescent effects.

(c) The hair conditioning compositions also, as discussed, render superior conditioning properties to the hair.

The system of this invention provides in-situ pearlescence in a cationic conditioning system and allows for the formation of pearlescence in the absence of conventional pearlescing agents. The pearlized effect is formed in-situ by the interaction of Richquat 150, Ammonyx 4 and sodium chloride. It may be enhanced by the presence of Polawax.

In summary, this invention discloses hair conditioning formulations which allow the in-situ formation of a stable pearlized appearance. The invention reveals the inclusion of specified components as critical to this achievement. Furthermore, the compositions simultaneously render superior conditioning properties to the hair, including body, manageability, and detangling without the simultaneous greasiness normally observed with hair conditioners.

We claim:

1. In a hair conditioner having a stable pearlescent effect and containing hair conditioning agents, emulsifiers, preservatives, and deionized water, wherein the improvement for providing pearlescence consisting of including therein between about 2.5% and about 7.5% by weight of stearamidopropyl dimethyl benzylammonium chloride, between about 2.0% and about 5.0% by weight of stearyl dimethyl benzylammonium chloride, and sufficient chloride salt to provide a minimum viscosity of 3,000 centipoise, and said hair conditioner having a pH between 3.0 and 4.0.

2. The hair conditioner of claim 1 in which said stearamidopropyl dimethyl benzylammonium chloride is about 5% by weight.

3. The hair conditioner of claim 1 in which said stearyl dimethyl benzylammonium chloride is about 3% by weight.

4. The hair conditioner of claims 1, 2, or 3 in which said chloride salt is sodium chloride and is present by about 0.5% by weight.

5. The hair conditioner of claim 1 including between about 0.40% and 0.75% of stearamidoethyl diethylamine by weight.

6. The hair conditioner of claim 5 in which said stearamidoethyl diethylamine is about 0.6%.

7. A hair conditioner providing a stable pearlescent effect consisting of
   (a) hair conditioning agents, emulsifiers, preservatives, perfume, and deionized water,
   (b) between about 2.5% and 7.5% by weight of stearamidopropyl dimethyl benzylammonium chloride, between about 2.0% and about 5.0% by weight of stearyl dimethyl benzylammonium chloride, about 0.25% and about 0.75% by weight of sodium chloride, and
   (c) an acid in sufficient quantity to give a pH between about 3.0 and 4.0.

8. The hair conditioner of claim 7 in which said stearamidopropyl dimethyl benzylammonium chloride is about 5.0% by weight, said stearyl dimethyl benzylammonium chloride is about 3.0% by weight, said acid is citric acid and is about 0.45% by weight, and said sodium chloride is about 0.5% by weight.

9. The hair conditioner of claim 7 in which said stearamidopropyl dimethyl benzylammonium chloride is about 5.0% by weight, said stearyl dimethyl benzylammonium chloride is about 3.0% by weight, said acid is citric acid and is about 0.45% by weight, and said sodium chloride is about 0.5% by weight and including 0.60% by weight of stearamidoethyl diethylamine.

10. The hair conditioner of claim 7 in which said hair conditioning agents include an agent for providing emolliency and lubricity selected from the group consisting of diethylaminoethyl stearamide, stearamidopropyl dimethylamine, stearamidoethyl diethylamine, and dimethylaminopropyl stearamide.

* * * * *